United States Patent
Granger et al.

[11] Patent Number: 5,968,076
[45] Date of Patent: Oct. 19, 1999

[54] CHANNEL-BODIED SURGICAL NEEDLE AND METHOD OF MANUFACTURE

[75] Inventors: Richard N. Granger, Huntington; Charles R. Sherts, Southport, both of Conn.

[73] Assignee: United States Surgical Corporation, Norwalk, Conn.

[21] Appl. No.: 08/843,548

[22] Filed: Apr. 18, 1997

Related U.S. Application Data

[63] Continuation of application No. 08/398,253, Mar. 3, 1995, abandoned.

[51] Int. Cl.⁶ .................................................. A61B 17/06
[52] U.S. Cl. ................................................................ 606/222
[58] Field of Search .......................... 606/222, 223, 606/224, 225, 226, 227, 147, 148, 139, 149

[56] References Cited

U.S. PATENT DOCUMENTS

| | | | |
|---|---|---|---|
| 279,693 | 6/1883 | Blinn | 606/223 |
| 2,560,162 | 7/1951 | Ferguson . | |
| 3,892,240 | 7/1975 | Park | 606/223 |
| 4,100,393 | 7/1978 | Luther | 219/121 |
| 4,237,892 | 12/1980 | Ritter et al. . | |
| 4,672,734 | 6/1987 | Kawada et al. . | |
| 4,785,868 | 11/1988 | Koenig, Jr. . | |
| 5,074,874 | 12/1991 | Yoon et al. | 606/224 |
| 5,224,955 | 7/1993 | West | 606/224 |
| 5,259,846 | 11/1993 | Granger et al. | 606/224 |
| 5,389,103 | 2/1995 | Melzer et al. | 606/139 |
| 5,425,737 | 6/1995 | Burbank et al. | 606/139 |
| 5,569,301 | 10/1996 | Granger et al. | 606/223 |

*Primary Examiner*—Michael Buiz
*Assistant Examiner*—Daphna Shai

[57] ABSTRACT

Channel-bodied surgical needles and surgical incision members are disclosed having a generally U-shaped cross-sectional body portion and a penetrating tip portion formed on at least one end thereof. Preferably, penetrating tip portions are formed at both ends of the channel-bodied portion. The surgical needle and/or surgical incision member may additionally includes apparatus engagement structure formed adjacent either end of the body portion and engagable with a suitable surgical suturing apparatus. The channel-bodied surgical needle and/or surgical incision member may additionally include securement structure for attachment of a length of suture material thereto. There is also disclosed apparatus for forming a channel-shaped body portion and the suture attachment structure. Additionally, methods for suturing tissue sections, particularly vascular tissue sections, with the channel-bodied surgical needle and the channel-bodied surgical incision members, are disclosed. Also, methods for forming the channel-bodied surgical needle and channel-bodied surgical incision member are disclosed.

21 Claims, 9 Drawing Sheets

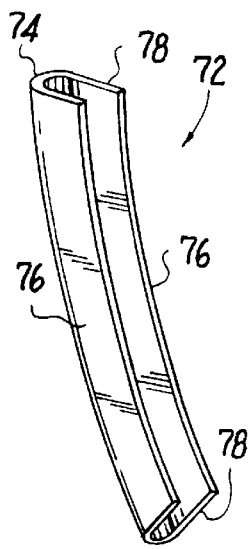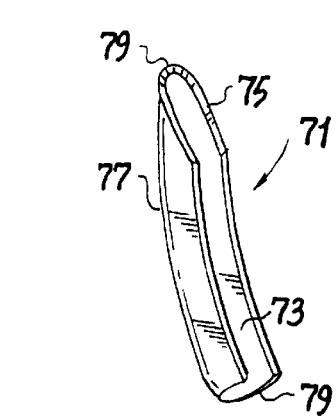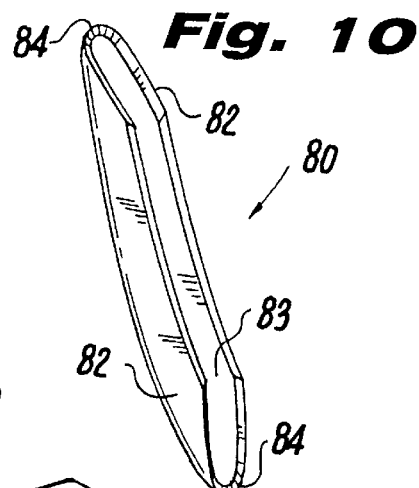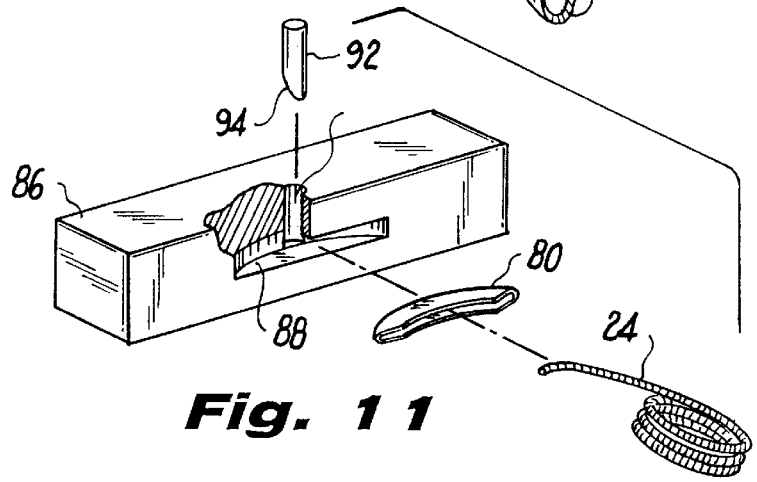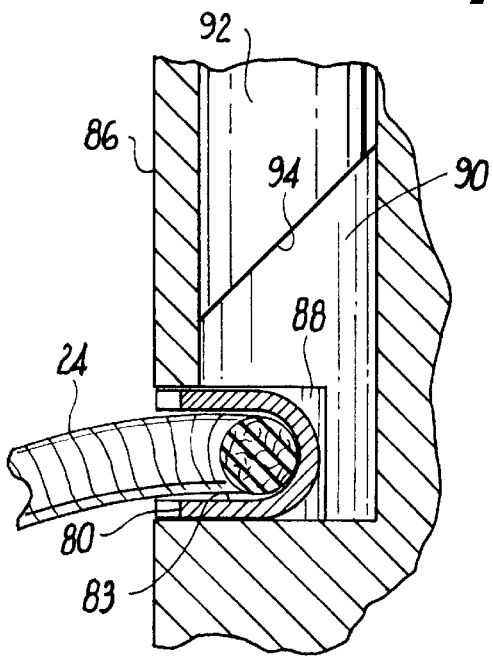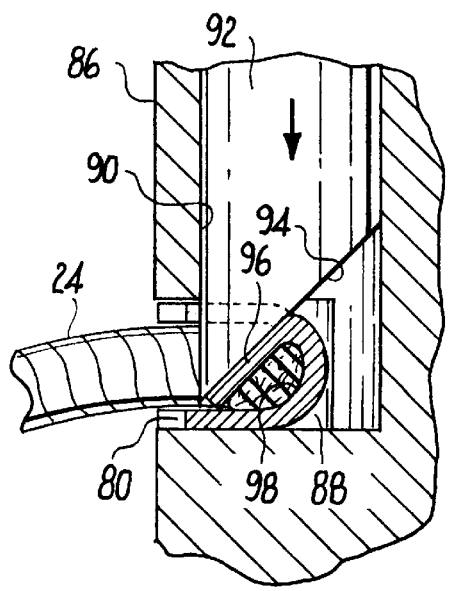

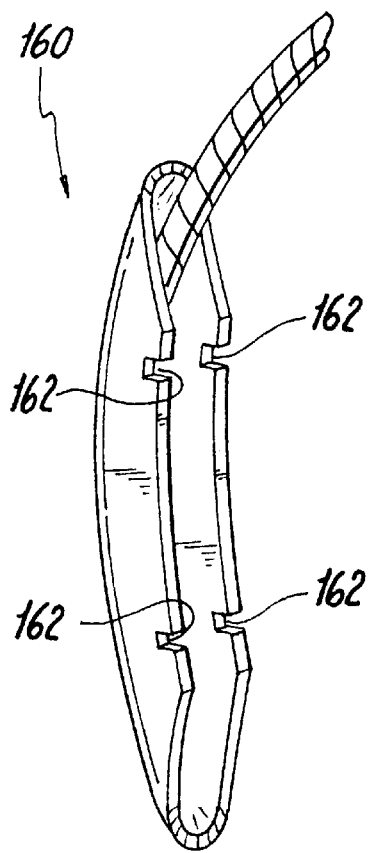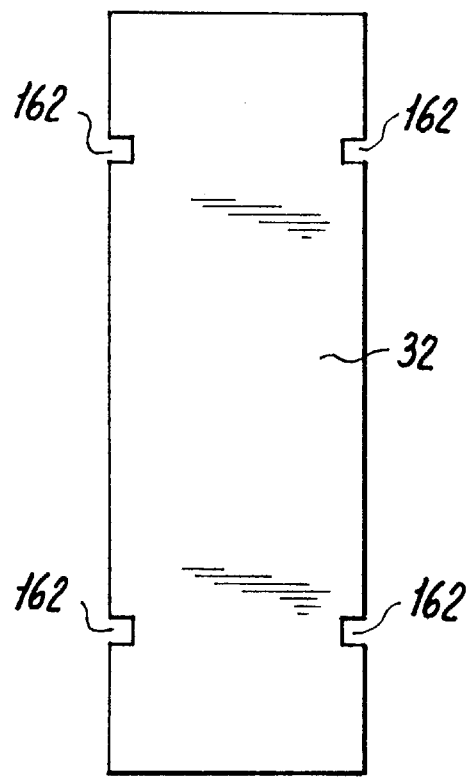
Fig. 24  Fig. 25

CHANNEL-BODIED SURGICAL NEEDLE AND METHOD OF MANUFACTURE

This is a continuation, of application Ser. No. 08/398,253 filed on Mar. 3, 1995, now abandoned.

BACKGROUND

1. Technical Field

This disclosure relates generally to surgical needles and, more particularly, to a surgical suturing needle having a channel-shaped body portion.

2. Description of Related Art

Surgical suturing needles are available in numerous types and sizes depending on the intended use or application. Surgical incision members are a type of surgical grade needle designed for use with surgical suturing instrumentation. Surgical incision members have points formed at either end and, preferably, a length of suture material attached intermediate the points. Typically, surgical incision members have a substantially uniform round cross-section, although other solid bodied cross-sections may be provided. Apparatus engagement structure may also be formed in a body portion of the surgical incision member to facilitate its use with a suitable surgical suturing apparatus. As used herein, the terms "surgical needle" and "surgical incision member" refer to fully formed surgical grade needles ready for suture attachment and use in surgical procedures. Further, as used herein, the term "needle blank" refers to a piece of needle stock at various stages of completion but not filly formed into a surgical grade needle or surgical incision member suitable for use during surgical procedures.

Solid bodied surgical incision members are disclosed in U.S. patent application Ser. Nos. 08/260,579, filed Jun. 16, 1994 entitled SURGICAL INCISION MEMBERS; and 29/024,594, filed Jun. 16, 1994 entitled SURGICAL INCISION MEMBER, the disclosures of which are incorporated by reference herein. Suitable apparatus for manipulation of surgical needles and surgical incision members are disclosed in U.S. patent application Ser. Nos. 06/954,013 filed Sep. 30, 1992 entitled SUTURING APPARATUS; 08/134,145 filed Oct. 8, 1993 entitled SURGICAL SUTURING APPARATUS WITH LOADING MECHANISM; 08/319,703 filed Oct. 7, 1994 entitled VASCULAR SUTURING APPARATUS; and 08/319,840 filed Oct. 7, 1994 entitled ENDOSCOPIC VASCULAR SUTURING APPARATUS.

During surgical procedures it is often necessary to join or rejoin tissue or vessels to form an anastomosis. Various methods of joining tissue or vascular tissues to create an anastomosis are used, such as, for example, suturing, stapling or clipping the tissue together. The anastomosis of vascular tissue involves particularly delicate and precise suturing in order to insure a secure and fluid tight seal. Given the very small size of typical vascular tissue, accurate and precise suturing on a small scale is imperative. Working in a highly magnified field, the surgeon uses a very small suturing needle having a length of suture material attached thereto to suture the vessels together. The suturing needle is typically grasped by a needle holder and passed through one vessel and then the opposite vessel. The procedure is repeated to thread or impart a series of stitches to the vessels to suture them together. Because of the extremely small size of the suturing needle used, typically on the order of ten thousandths of an inch in diameter, and the highly magnified field, handling problems may arise while manipulating the suturing needle through the vascular tissues. Drawing the needle and suture through a vessel requires the controlled and accurate release and acquisition of the needle and suture during the procedure. Precise control of the needle is often difficult when using typical needle holders. Thus surgical suturing apparatus which manipulate either surgical needles or surgical incision members are particularly useful in vascular surgery. They can provide accurate and reliable transfer of the needles or incision members through vascular tissue, particularly in small operating fields.

Care must be taken to ensure only a minimal puncture is performed and that the tissue is not damaged as the suture is drawn through. Round punctures in vascular tissues can take longer to heal than a non-circular incision or cut. Further, when using round-bodied surgical needles, the size of the needle and suture should be carefully matched to ensure the suture does not tear tissue and to prevent fluid leakage from the vessel. Accordingly, a need exists for a surgical needle and/or surgical incision member which penetrates tissue in a less traumatic manner than a conventional needle. It would be desirable to make a more incision-like penetration of the tissue to facilitate healing.

Surgical needles and/or surgical incision members typically require several processes to form the finished product. These processes may include curving and cutting needle stock to form needle blanks, altering or refining the tip configurations and curvature radius, punching or drilling the blank to form a suture hole and/or notching the blank to provide engaging structure for cooperative instrumentation.

Due to the complexity of forming round-bodied surgical needles and surgical incision members, the manufacture of surgical incision members may become complicated and costly. For example, one commonly used method of manufacturing a round-bodied surgical incision member is by a process called metal injection molding or "MIM". The MIM manufacturing process tends to be costly and thus may adversely affect the otherwise desirable characteristics and traits of a surgical suturing apparatus utilizing surgical incision members.

It would be desirable to have a surgical suturing needle or incision member which can be produced with reduced cost and effort. It also would be desirable to have a vascular surgical suturing needle which is particularly suited to microscopic suturing of vascular tissues and which is capable of penetrating, and drawing a suture through, vascular tissue sections with minimal trauma to the tissue. It would also be desirable to have an inexpensive surgical suturing needle or surgical incision member which is easily handled by a surgical suturing apparatus.

SUMMARY

A surgical suturing needle is disclosed having a channel shaped body portion, preferably of a U-shaped cross-section, and a penetrating tip portion formed on at least one end. As used herein, the phrase "channel-bodied surgical needle" is intended to refer to a needle having a substantially open-centered body portion. Preferably, penetrating tip portions are formed at both ends of the channel-bodied surgical needle with a suture being attached thereto intermediate the tip portions. The channel-bodied surgical needle may also include apparatus engagement structure which, in one embodiment, includes a pair of holes formed adjacent either end of the channel-shaped body portion. The holes are engagable with corresponding structure on a suitable surgical suturing apparatus to facilitate transfer of the needle between jaws thereof. In another embodiment, the apparatus engagement structure is formed as crimps or notches in the side walls of the channel-shaped portion and adjacent either end. When the channel-bodied surgical needle includes penetrating tip portions at either end it forms a "channel-bodied surgical incision member".

Suture attachment structure is located between the penetrating tip portions to secure a length of suture material to the channel-shaped body portion. This structure may include an inwardly directed flap cut from a side wall which serves to crimp an end portion of a suture within the channel-shaped body portion. Alternatively, in a second embodiment, the suture attachment structure is formed as a pinched or inwardly directed bulging portion in the channel-shaped body portion which serves to crimp a suture therein. In a further alternative embodiment, the suture attachment structure includes a tab portion projecting from a side wall. The tab portion is foldable within the channel to secure a length of suture material therein. Preferably, the suture attachment structure is formed within the channel-shaped body portion at a location substantially intermediate either end thereof. Welds, glue and the like also may be used to secure the suture within the channel-shaped body portion.

Also disclosed is an apparatus for forming a channel-bodied surgical needle, or a channel-bodied surgical incision member, which generally includes a forming die for producing the channel-shaped body portion of the needle. The forming die generally includes a first member having a blade or mandrel projecting therefrom. A second member is provided which generally includes a ledge for support of a needle blank and a slot positioned beneath the ledge for receipt of the mandrel therein. As the mandrel is forced down against the needle blank, it forces the needle blank into the slot thereby forming the channel-shaped body portion in the needle blank.

Structure is also provided for imparting apparatus engagement structure to the needle blank including providing a pre-stamped blank having holes adjacent either end thereof or providing a die or other suitable structure for crimping or coining side walls of a channel-bodied needle portion. Additionally, suture attachment structure is provided in the form of a crimping or suture attachment die which has a channel therein for receipt of a channel-bodied surgical needle. The suture attachment die has a cutting wedge or pin which, when a length of suture material is positioned within the channel-shaped body portion, is forced down to cut a flap in the side wall of the channel-shaped body portion. The flap is folded inwardly against the length of suture material to firmly secure the suture material within the surgical needle. Alternatively, one or more dies for crimping a center portion of the surgical of the channel-shaped body portion to crimp a suture without creating such a flap may be provided.

There is also disclosed a method of suturing body tissue utilizing a channel-bodied surgical needle as well as a method of suturing vascular tissue utilizing a channel-bodied surgical incision member. The latter method generally includes providing a channel-bodied surgical incision member having a length of suture material attached thereto and positioning the channel-bodied surgical incision member within suitable suturing apparatus having needle engagement structure. The channel-bodied surgical incision member is forced against a tissue section to pierce the tissue section and cut a flap of tissue in the side wall. As the channel-bodied surgical incision member is passed through the tissue section, the suture material lies substantially within the channel-shaped body portion to minimize tissue trauma. The surgical suturing apparatus draws the surgical incision member and length of suture material through the tissue section without increasing the size of the cut tissue flap. The size of the surgical incision member can be closely matched to the size of the suture, and the creation of a flap rather than a punctured hole in tissue provides good sealing of the tissue around the suture. In the case of a surgical incision member the method also includes passing the surgical incision member back and forth through tissue, piercing the tissue alternately with each end of the channel bodied surgical incision member.

There is also provided a method of forming a channel-bodied surgical incision member or a channel-bodied surgical needle. A method generally includes providing a flat needle blank, preferably with ends pre-ground or preformed with cutting edges and with apparatus engagement structure. The needle blank is folded substantially in half to create a U-shaped channel-shaped body portion and may be ground to form cutting edges at either end thereof. Once the needle blank has been formed with a channel-shaped body portion, cutting ends at either end thereof and suitable apparatus engagement structure a channel-bodied surgical incision member has been formed. There are also disclosed a channel-bodied surgical needle and channel-bodied surgical incision member formed on the above apparatus and according to the above methods.

BRIEF DESCRIPTION OF THE DRAWINGS

Various embodiments are described herein with reference to the drawings, wherein:

FIG. 9 is a perspective view of a channel-bodied needle blank;

FIG. 9a is a perspective view of a channel-bodied surgical needle having a single tissue penetration end prior to suture attachment;

FIG. 10 is a perspective view of a channel-bodied surgical incision member having tissue penetrating tips formed at either end thereof prior to suture attachment;

FIG. 11 is a perspective view of an apparatus for imparting suture attachment structure to a channel-bodied surgical needle or incision member, FIG. 12 is partial cross-sectional view of the apparatus of FIG. 11 with a suture and surgical incision member inserted therein;

FIG. 13 is a view similar to FIG. 12 illustrating a die cutting a portion of the body portion to secure a suture within a channel-bodied surgical incision member or needle;

FIG. 24 is a perspective view of a surgical incision member with apparatus engagement notches;

FIG. 25 is a plan view of a stamped needle blank with stamped notches for forming the surgical incision member of FIG. 24;

DESCRIPTION OF PREFERRED EMBODIMENT(S)

Figure 1:
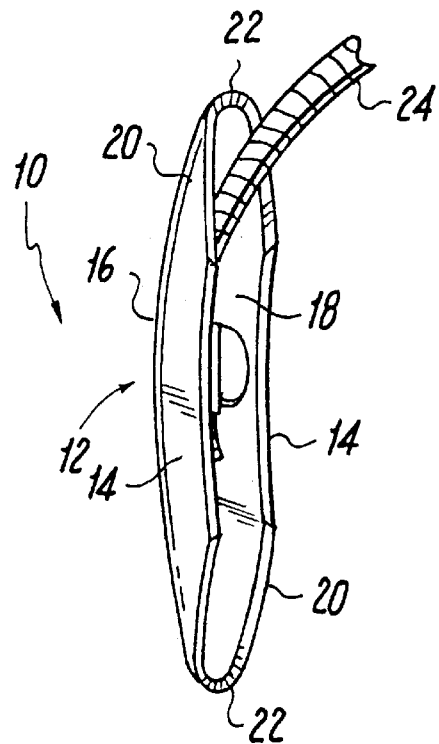
FIG. 1 is a perspective view of a preferred embodiment of a channel-bodied surgical incision member.

Referring now to FIG. 1, there is shown a hollow channel-bodied surgical incision member which may be particularly suited for use in suturing of vascular tissue sections. As used herein, the term "channel-bodied", "channel-shaped body" or "channel-shaped cross-section" refers to a hollow body having a cross-sectional area such that the walls of body portion form a needle having a substantially open, hollow body over substantially the entire length of the needle. Preferably, the channel-bodied needle or surgical incision member is curved, as shown. Alternatively, it is contemplated that the channel-bodied needle or surgical incision member could be straight or substantially straight over its length.

Although the discussion herein below is specifically oriented to the use of the present surgical incision member with a surgical suturing apparatus in vascular surgery, other uses are contemplated including manual suturing and suturing with conventional needle holders in general surgery. Thus, while the present description is primarily in terms of endoscopic surgery and vascular surgery, it should be understood that the surgical needles and incision members may find use in general surgery as well.

Channel-bodied surgical incision member 10 generally includes a body portion 12 having a pair of generally parallel sides 14 and a generally curved base 16 connecting adjacent sides 14. Sides 14, along with base 16, define a channel 18 extending substantially the length of channel-bodied surgical incision member 10. Channel-bodied surgical incision member 10 may be formed of various suitable biocompatable needle stock materials such as, for example, stainless steel, etc. Body portion 12 preferably has a U-shaped cross-section although various other cross-sections are contemplated. A preferred length of a finished channel body needle suitable for use in vascular surgery is on the order of approximately 0.350 inches. Channel-bodied surgical incision member 10 further includes a tissue penetrating end or tip 20 formed on each end of body portion 12. Tissue penetrating ends 20 are preferably formed with sharp cutting edges 22 to facilitate piercing a tissue section. When forced against tissue, cutting edges 22 cut a flap of tissue rather than forming a puncture hole. Channel-bodied surgical incision member 10 is designed to facilitate passing a length of suture material such as, for example, suture 24 through a vascular tissue section with minimal disruption of the vascular tissue.

Figure 2:
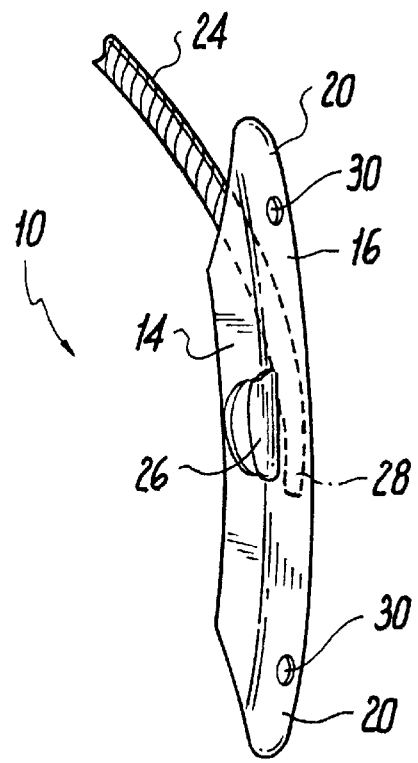
FIG. 2 is an alternate perspective view of a channel-bodied surgical incision member similar to the surgical incision member of FIG. 1.
Figure 14:
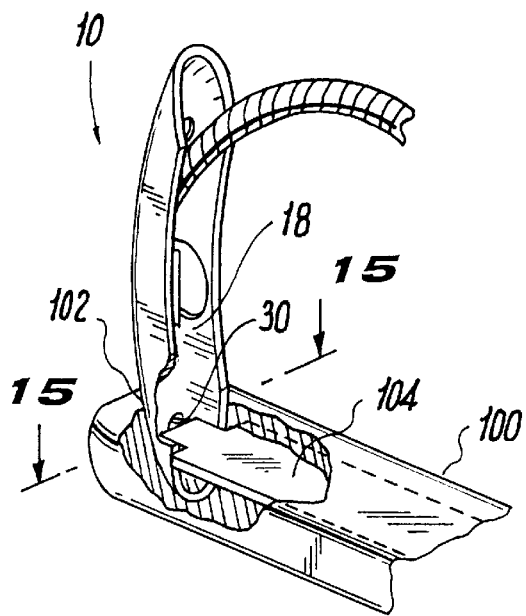
FIG. 14 is a perspective view of the channel-bodied surgical incision member and a portion of an arm or jaw of a suturing apparatus illustrating the apparatus engagement structure of the channel-bodied surgical incision member cooperating with corresponding structure on the jaw.
Figure 15:
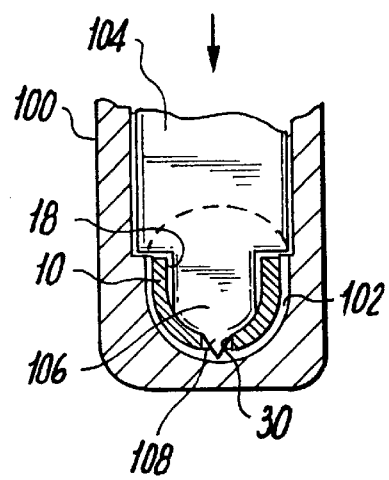
FIG. 15 is a cross-sectional view taken along line 15—15 of FIG. 14.
Figure 16:
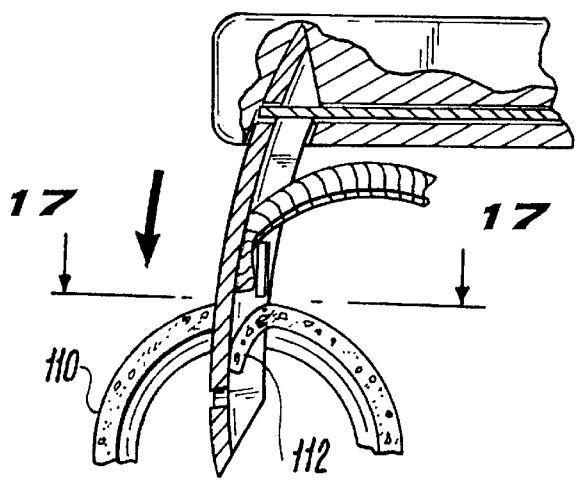
FIG. 16 is a perspective view partially shown in section illustrating the channel-bodied surgical incision member piercing a vascular tissue section.

Referring now to FIG. 2, channel-bodied surgical incision member 10 includes apparatus engagement structure and suture attachment structure. In this embodiment, the suture attachment structure is preferably in the form of an inwardly directed flap portion 26 formed in one side 14. Flap 26 serves to pinch an end 28 of suture 24 within channel 18, as shown. In order to facilitate holding channel-bodied surgical incision member 10 and passing the surgical incision member between arms or jaws of a surgical suturing apparatus (see FIG. 14), channel-bodied surgical incision member 10 further includes apparatus engagement structure which cooperates with corresponding needle engaging structure in a surgical suturing apparatus (FIGS. 14–16). In this embodiment, the apparatus engagement structure is provided in the form of holes 30 formed in base 16. Preferably, one hole 30 is formed adjacent either end of base 16 as shown. Alternatively, holes 30 may be formed at various locations, such as, for example, in sides 14. Notches and other comparable apparatus engagement structure are also contemplated, such as notches coined into base 16 or into the edges of side walls 14. Preferably, when apparatus engagement structure is produced in the form of holes, the holes have a diameter on the order of 0.01 inches to 0.02 inches and more preferably about 0.016 inches.

Figure 3:
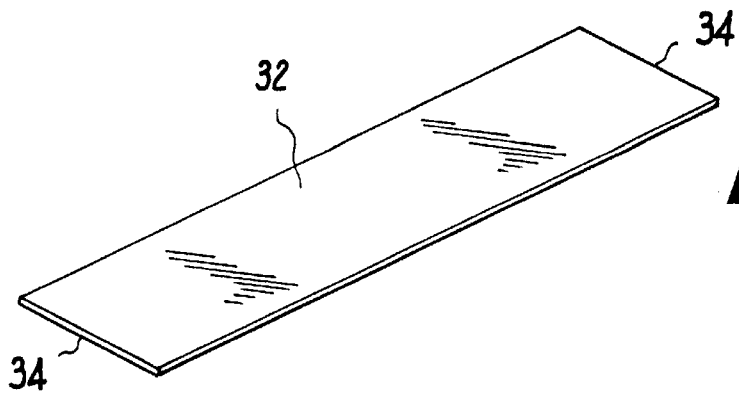
FIG. 3 is a perspective view of a stamped needle blank.
Figure 4:
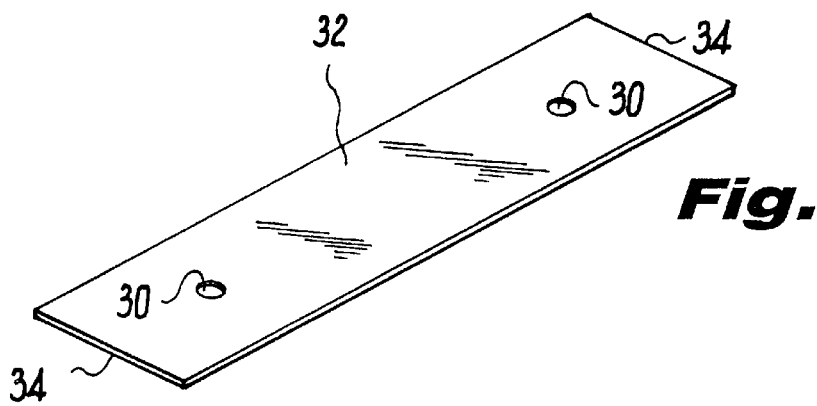
FIG. 4 is a perspective view similar to FIG. 3, illustrating apparatus engagement structure stamped in the needle blank.
Figure 5:
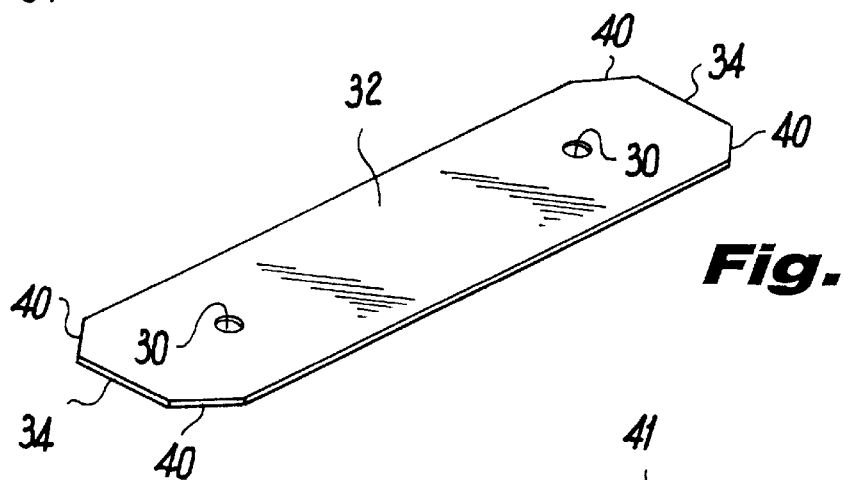
FIG. 5 is a perspective view of a piece of needle stock material stamped to form cutting or beveled edges at either end thereof.
Figure 5A:
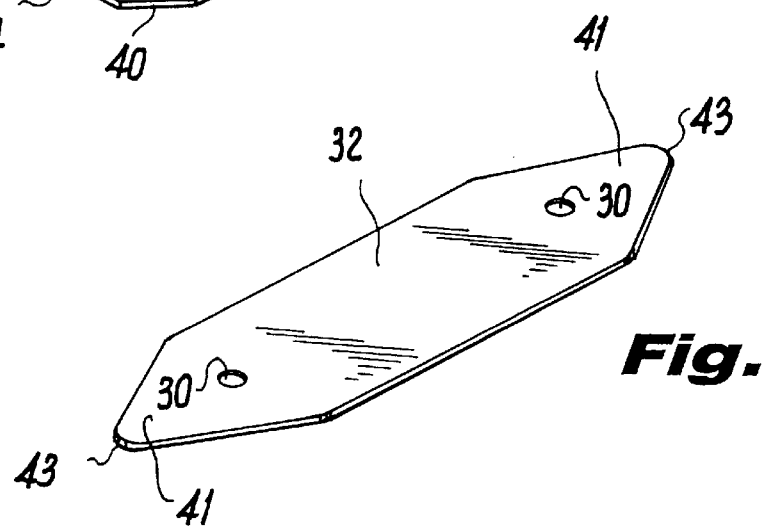
FIG. 5a is a perspective view of needle stock material stamped to form substantially pointed ends with cutting edges.
Figure 6:
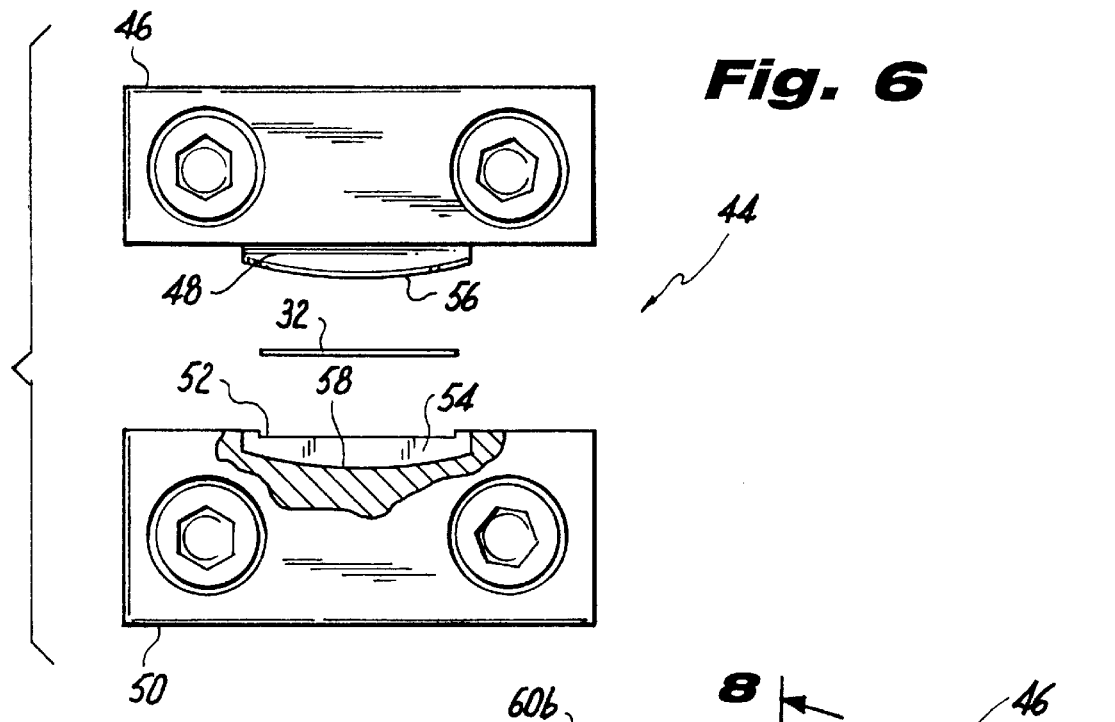
FIG. 6 is a side elevational view, partially shown in section, of a channel body forming die.

Referring now to FIGS. 3–8, and initially to FIGS. 3–5a, a preferred method of forming a channel-bodied surgical incision member 10 win be described. A needle blank such as, for example, flat rectangular needle blank 32 is stamped out of needle stock material. Needle blank 32 may be substantially rectangular, as shown in FIG. 3, in which case one or both ends of the blank preferably are ground to form pointed ends, either before or after forming the rectangular blank into a channel-bodied structure as described below. Additionally, as shown in FIG. 4, apparatus engagement structure such as, for example, holes 30 may be stamped or punched into the needle blank 32 prior to forming into a channel-bodied structure. Alternatively, as shown in FIG. 5, needle blank 32 can be stamped to have cut corners 40. Preferably, cut corners 40 and ends 34 are beveled or ground to produce sharp cutting edges. Alternatively, corners 40 and ends 34 may be stamped to form beveled sharp cutting edges at the time the flat blank is formed. It is also contemplated that pointed cut corners 40 could join to form a substantially pointed tip at each end of blank 32 without a straight transverse edge 34, or that the length of transverse edge 34 could be varied to obtain different tip configurations. It also is contemplated that corners 40 could be stamped to provide a curved corner having one or more radii of curvature. By way of example only, FIG. 5a illustrates an alternate needle blank 32 having substantially pointed ends 41 with rounded tips 43. Cutting edges may be stamped into the edges of the pointed tip. In the embodiment of FIG. 5, the needle blank includes apparatus engagement apertures 30. Referring now to FIG. 6, there is disclosed a channel forming die for forming the channel body portion 12 in needle blank 32. Channel forming die 44 generally includes a first portion 46 having a forming mandrel 48 positioned therein and a second portion 50 having a needle blank ledge 52 for support of a needle blank 32. Second portion 50 further includes a forming slot 54 for receipt of mandrel 48.

In order to form a curved channel-bodied surgical incision member, mandrel 48 preferably has an arcuate edge 56 and channel 54 has an arcuate base 58. Thus, when needle blank 32 is positioned on ledge 52 and compressed between first portion 46 and second portion 50 it will assume the arcuate shape of edge 56 and base 58. Preferably, forming die 44 is configured to impart an arcuate radius on the order of 0.775 inches to the needle blank. It also is contemplated that the leading edge 56 of mandrel 48 and base 58 of slot 54 may be straight in order to produce a straight channel-bodied needle, as opposed to a curved channel-bodied needle. A straight surgical incision member may be desirable for use with a suturing apparatus having straight parallel jaw structure.

Figure 7:
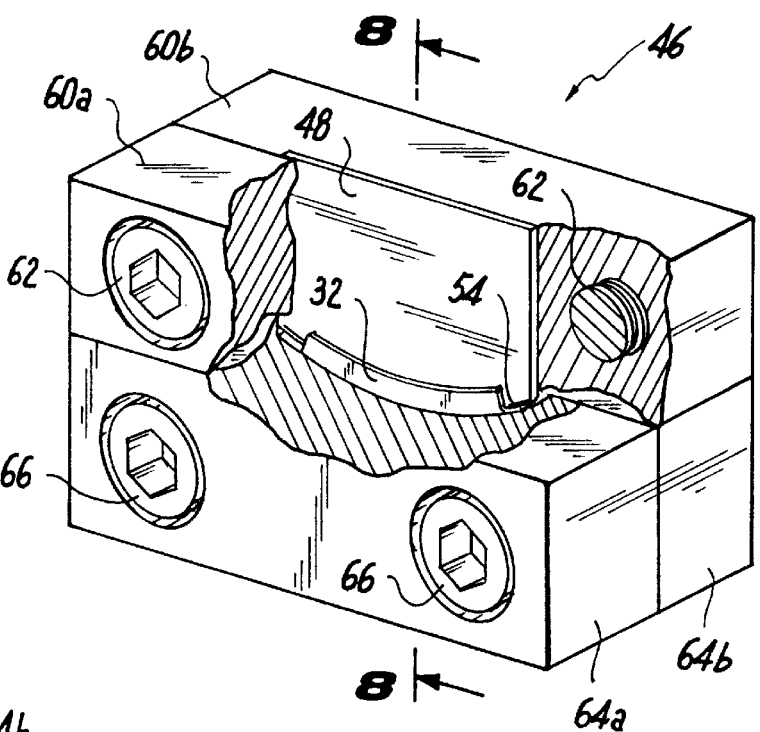
FIG. 7 is a perspective view of the channel body forming die, partially shown in section.

Referring now to FIG. 7, first portion 46 generally includes first and second sides 60A and 60B which are configured to clamp mandrel 48 therebetween by means of a pair of bolts 62. Second portion 50 also includes first and second halves 64A and 64B, held together by a pair of bolts 66.

Figure 8:
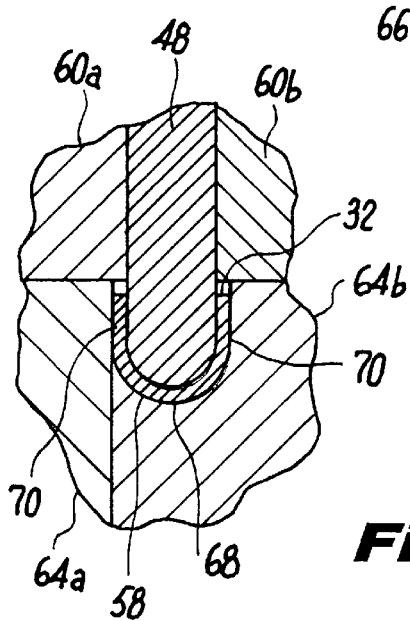
FIG. 8 is a partial cross-sectional view taken along the line 8—8 of FIG. 7.

As shown in FIG. 8, channel 54 generally has a U-shaped cross-section including an arcuate base 68 for receipt of edge 56 and a pair of parallel sides 70. Referring again to FIG. 6, a needle blank 32 is positioned in registration on ledge 52. Channel forming die 44 is positioned within a suitable press or forming apparatus and first portion 46 is positioned above second portion 50. First portion 46 is forced downwardly towards second portion 50 causing mandrel 48 to force needle blank 32 downwardly within slot 54. As needle blank is forced downwardly into slot 54 by mandrel 48, it is forced formed into an arcuate shape in both the longitudinal and cross-sectional directions (FIGS. 7 and 8). Arcuate edge 56 of mandrel 48 along with arcuate surface 58 of channel 54 serve to form the longitudinal curvature in needle blank 32.

As best shown in FIG. 8, arcuate base portion 68 along with parallel sides 70 serve to impart the channel and U-shaped cross-sectional area to needle blank 32 in response to mandrel 48. Upon separating portions 46 and 50, there is formed a channel-bodied needle blank 72 as best shown in FIG. 9. Channel-bodied needle blank 72 generally includes a base portion 74 having the shape imparted to it by mandrel 48 and arcuate base portion 68. Additionally, blank 72 has a pair of substantially parallel sides 76.

As noted hereinabove, needle blanks to be formed into channel-bodied needles or surgical incision members may be ground or stamped to have cutting edges at either ends or at one end either before or after the channel forming operation. Channel-bodied needle blank 72 of FIG. 9 has a pair of flush ends 78, as would be achieved with a substantially rectangular needle blank (see FIGS. 3 and 4). Blank 72 may then be taken to suitable grinding machinery to impart ground edges and points.

A channel-bodied needle having a tissue penetrating end on only one end thereof is best illustrated in FIG. 9a. Channel-bodied needle 71 also has a U-shaped configuration including a channel 73 defined by sides 75 and base 77. As noted, channel-bodied needle 71 has a single tissue penetrating end or tip 77 having a cutting edge 91 formed thereon. An opposite end 79 of needle 71 remains flush for subsequent suture attachment, such as by crimping a suture tip within end 79, or when used with a suitable surgical instrument, provides a surface against which channel-bodied needle 71 may be pushed to force it through tissue.

A ground and sharpened channel-bodied surgical incision member is illustrated in FIG. 10. Incision member 80 generally includes a pair of tissue penetrating ends 82 each having cutting edges 84 ground therein.

Various methods may be utilized to attach a length of suture material to channel-bodied needles and/or surgical incision members. Referring now to FIG. 11, there is disclosed a suture attachment die 86 which is configured for crimping a length of suture material, such as, for example, suture 24 within a channel-bodied needle or surgical incision member. Suture attachment die 86 generally includes a needle holding channel 88 which is configured to conform generally to the shape of a channel-bodied surgical incision member and to position the needle or surgical incision member for suture attachment. Suture attachment die 86 further includes a bore 90 which is oriented substantially perpendicular to channel 88 and intersects channel 88. A side punch 92 having a sharp cutting tip 94 is provided and is slidable within channel 90 so as to engage an edge of a surgical incision member disposed therein.

As shown in FIGS. 12 and 13, in operation, suture 24 is initially longitudinally disposed within a body channel 18 in channel-bodied surgical incision member 80 positioned within holding channel 88. Suture attachment die 86 is then engaged with a suitable press or punch for forcing die 92 through bore 90. As shown, in an initial position, die 92, and thus cutting tip 94, is at a position remote from holding channel 88. Referring now specifically to FIG. 13, as die 92 is forced down within bore 90, cutting tip 94 engages a side wall 82 and cuts a portion of the side wall to form an inwardly directed flap 96. Side punch 92 is forced down sufficiently to cause flap 96 to crimp a portion of suture material 98 within the body portion 82 of channel-bodied surgical incision member 80. Once flap 92 has been compressed against portion 98 and suture 24, side punch 92 may be retracted to free the now suture loaded channel-bodied needle 80 and attached suture 24 from suture attachment die 86. In the resulting needle-suture attachment, the tip of the suture is positioned behind flap 96 with the body of the suture extending around the flap in the hollow needle body (compare FIGS. 2 and 16).

At this point a fully formed channel-bodied surgical incision member having a length of suture material affixed thereto may be sterilized or otherwise treated for use in a surgical operation. As noted hereinabove, channel-bodied surgical incision member 10 is particularly suited for use with a surgical suturing apparatus having needle engaging structure and which is designed to rapidly and efficiently transfer a channel-bodied surgical incision member repeatedly between a pair of jaws, such as the apparatus disclosed in the various U.S. Patent Applications incorporated by reference hereinabove.

Referring now to FIGS. 14–17 and initially to FIG. 14, in order to use channel-bodied surgical incision member 10 in a surgical suturing operation, such as, for example, the suturing of vascular tissues, channel-bodied surgical incision member 10 is loaded within an arm or jaw of a suitable surgical suturing apparatus, such as, for example, jaw 100. Channel-bodied surgical incision member 10 is inserted within jaw 100 by inserting it within a recess 102 in the jaw, where engaging hole 30 may be engaged with a suitable needle engaging member 104 disposed within jaw 100.

Channel-bodied surgical incision member 10 provides a unique configuration for engagement with cooperating structure on a surgical suturing apparatus. Referring now to FIG. 15, as needle engaging member 104 is advanced within jaw 100, a tip of needle engaging member 104, having a shape generally configured to conform to channel 18, such as tip 106, is moved within channel 18. Tip 106 additionally includes a projecting pin or point 108 which is configured and dimensioned to engage hole 30 and secure channel-bodied surgical incision member 10 within jaw 100.

Figure 17:
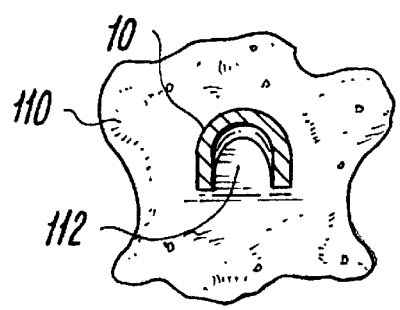
FIG. 17 is a view taken along line 17—17 of FIG. 16 illustrating the incision made by the surgical incision member.

As illustrated in FIGS. 16–17, channel-bodied surgical incision member 10, positioned with jaw 100 of a suturing apparatus, may be utilized to pierce and suture one or more tissue sections such as, for example, vascular tissue section 110. Upon piercing tissue section 110, sharp cutting edges 22 on tissue penetrating ends 20 cut a flap of tissue 112 within vessel wall 110 (FIG. 16). As best shown in FIG. 17, the portion of vessel wall 110 cut, flap 112, generally conforms to the inner shape of channel 18. The cutting of a flap of tissue 112 rather than forming a puncture hole may be desirable to promote healing since a channel cut or half moon slice may be less traumatic than a round puncture, particularly in vascular tissue. Upon passing channel-bodied surgical incision member 10 through vessel wall 110, a portion of suture 24 is folded or forced within channel 18. Thus, on passing through vessel wall 110 or other tissue sections, suture 24 lies within channel 18 and does not tear or enlarge cut flap 112 formed by sharp cutting edges 22. In addition, the cut flap may promote a seal of vascular tissue about the suture. Channel-bodied surgical incision member 10 may be repeatedly passed back and forth between a pair of jaws 100 by alternatively engaging holes 30 with needle engaging member 104 to repeatedly draw suture material 24 through one or more tissue sections.

Figure 18:
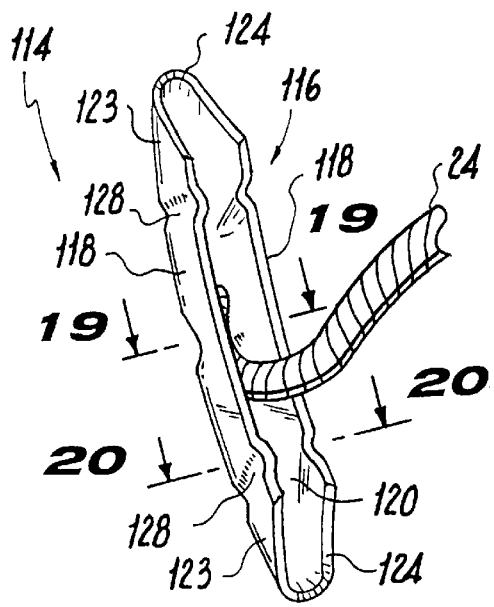
FIG. 18 is an alternate embodiment of the channel-bodied surgical incision member.
Figure 19:
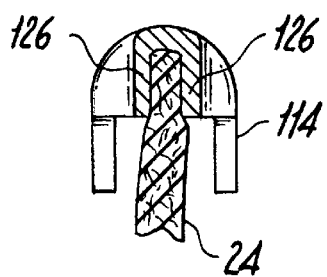
FIG. 19 is a cross-sectional view taken along line 19—19 of FIG. 18 and illustrating suture attachment structure.

Referring now to FIG. 18, there is disclosed an alternate embodiment of a channel-bodied surgical incision member. Similar to channel-bodied surgical incision member 10, channel-bodied surgical incision member 114 generally includes a body portion 116 having a pair of sides 118 which define a channel 120 therein. Channel-bodied surgical incision member 114 further includes a pair of tissue penetrating ends 123 having sharp cutting edges 124 formed thereon and suture attachment structure. In this embodiment the suture attachment structure is provided in the form of a reduced cross-sectional area or inwardly directed crimp formed in sides 118. Referring to FIG. 19, a cross-section view taken along lines 19—19 of FIG. 18, inwardly directed bulges 126 serve to crimp a portion of length of suture material 24 therebetween thereby securing suture material 24 with channel-bodied surgical incision member 114. As will be appreciated, crimping sides 118 also is conducive to attaching suture 24 in substantially perpendicular orientation relative to body portion 116, should such attachment be desired.

Figure 20:
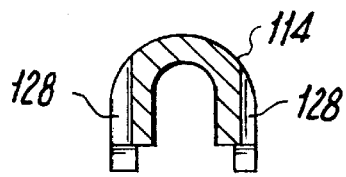
FIG. 20 is a cross-sectional view taken along line 20—20 of FIG. 18.

Channel-bodied surgical incision member 114 also includes apparatus engagement structure. In this embodiment the apparatus engagement structure is in the form of reduced cross-sectional area adjacent either end of body portion 116 and is generally formed by crimping. Referring now to FIG. 20, a cross-section view taken along lines 20—20 of FIG. 18, reduced cross-sectional areas 128 provide grooves along an outer edge of channel-bodied surgical incision member 114 for engagement with suitable needle engaging members of surgical suturing apparatus, such as, for example, blades, etc.

Figure 21:
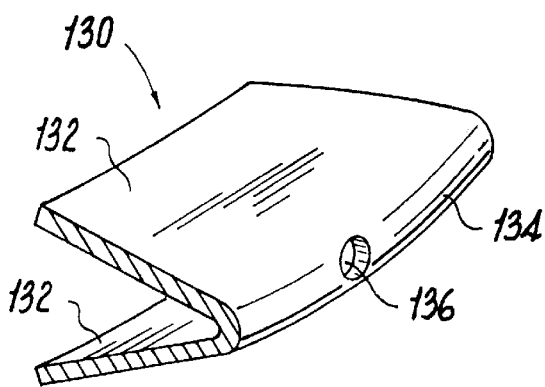
FIGS. 21–23 are perspective cross-sectional views illustrating further cross-sectional configurations for the channel-bodied surgical needle or incision member.
Figure 22:
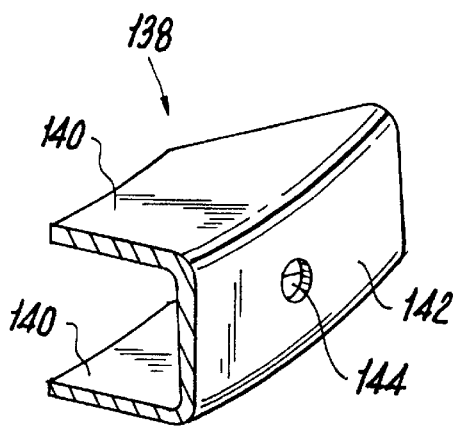

While the preferred embodiments of channel-bodied surgical incision member includes a generally U-shaped cross-sectional area various other cross-sectional areas are contemplated and may be useful for various procedures or instruments. For example, when a very narrow flap of tissue or incision is required, a channel-bodied needle having a v-shaped cross-section such as, for example, channel-bodied structure 130 shown in FIG. 21 may be provided. Channel-bodied structure 130 has a pair of sides 132 joined by a relative narrow base 134 formed thereon. Channel-bodied structure 130 may additionally include apparatus engagement structure in the form of one or more holes 136. Similarly, where a rectangular cross-section would be desired, there is provided a channel-bodied structure 138 as best shown in FIG. 22 having a pair parallel sides 140 and a base portion 142 formed substantially perpendicular to sides 140. Additionally, channel-bodied structure 138 may include apparatus in engagement structure in the form a hole or holes 144.

Figure 23:
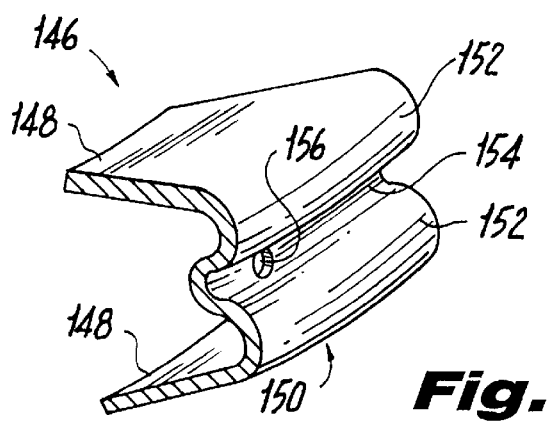

A further alternate embodiment having cross-sectional area in the form of a W, is best illustrated in FIG. 23. Channel-bodied structure 146 generally includes a pair of sides 148 having a base 150. Base 150 generally includes a pair of inwardly facing concave portions 152 connected by an outwardly facing concave portion 154. Preferably, apparatus engagement structure in the form of a hole 156 is formed in concave portion 154. Alternatively, hole 156 may be formed in one or both concave surfaces 152. Depending upon the desired structure, i.e., either a surgical needle or a surgical incision member, cutting edges and tissue penetrating ends may be formed either in a flat blank or in a blank formed into a channel-bodied needle portion. Cutting edges may be stamped or ground into opposite ends of the channel-bodied blank or alternatively channel-bodied needle may have a tissue penetrating end at only one end thereof.

Referring to FIG. 24, a further alternative embodiment is shown. Surgical incision member 160 shown in FIG. 24 is substantially similar to prior embodiments. However, surgical incision member 160 includes apparatus engagement notches 162 for engaging blades or other structure of a suturing apparatus to hold surgical incision member 160 in the jaws of the instrument. Referring to FIG. 25, a needle blank 32 is shown with notches 162 stamped therein. Alternatively, notches 162 may be coined or ground in blank 32 or in surgical incision member 160 after the blank is curved into the shape shown in FIG. 24. Preferably, blank 32 of FIG. 25 is curved around a mandrel and pointed tip portions with cutting edges are ground into the curved needle blank to provide a surgical incision member having pointed tips with cutting edges. In use, engagement blades of a suitable suturing apparatus engage notches 162 to control passing of surgical incision member 160 back and forth between jaws or arms of the instrument.

Figure 26:
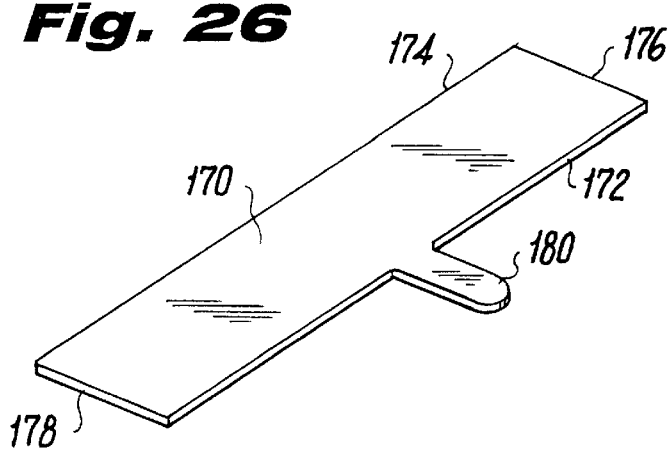
FIG. 26 is a perspective view of an alternate channel-bodied surgical needle blank incorporating alternate suture attachment structure.

Referring now to FIG. 26, a further alternative needle blank is shown. Needle blank 170 generally includes first and second longitudinal side edges 172 and 174, respectively, and transverse end edges 176 and 178. Alternate blank 170 is suitable for forming into a channel-bodied surgical needle or channel-bodied surgical incision member and includes unique suture attachment structure in the form of a tab 180 projecting from first longitudinal side edge 172. Tab 180 is utilized to crimp a portion of a suture within a channel of the channel-bodied surgical needle or channel-bodied surgical incision member formed from needle blank 170.

Figure 27:
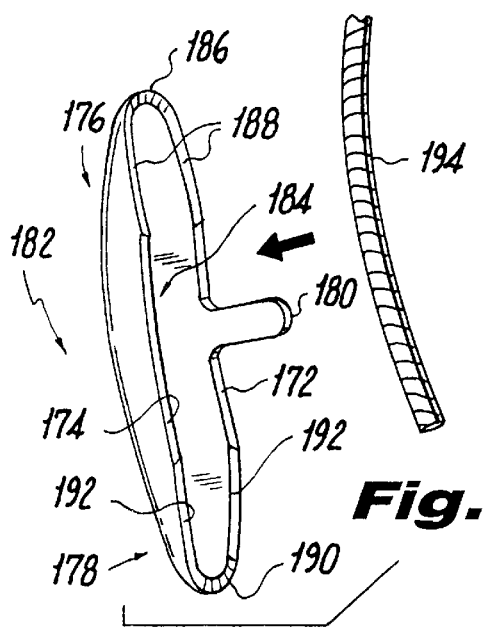
FIG. 27 is a perspective view of a channel-bodied surgical incision member formed from the needle blank of FIG. 26 and ready to receive a suture for attachment thereto.

Referring now to FIG. 27, there is disclosed a channel-bodied surgical incision member formed from needle blank 170. Channel-bodied surgical incision member 182 is formed in the manner described hereinabove and includes a channel 184 formed between first and second longitudinal side edges, 172 and 174, respectively. Preferably, transverse end edges 176 and 178 are ground or otherwise processed in the manner described hereinabove to result in a cutting or sharpened tip portion 186 and unsharpened tapered portions 188 at transverse end edge 176 and cutting or sharpened tip portion 190 and unsharpened tapered portion 192 at the opposite transverse end edge 178. Sharpened tip portions 186 and 190 form cutting edges for slicing and penetrating tissue. Once needle blank 170 has been formed into channel-bodied surgical incision member 182, and ground or sharpened to form sharpened tip portions 186 and 192, channel-bodied surgical incision member 182 is ready to receive a length of suture, such as, for example, suture 194 for securement within channel 184.

Figure 28:
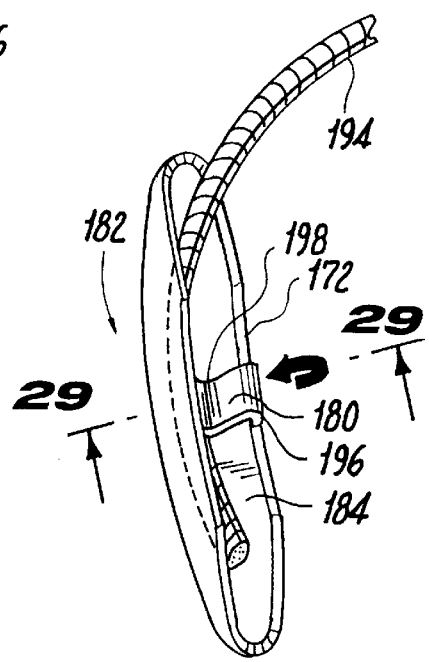
FIG. 28 is a perspective view of the channel-bodied surgical incision member of FIG. 27 during suture attachment.
Figure 29:
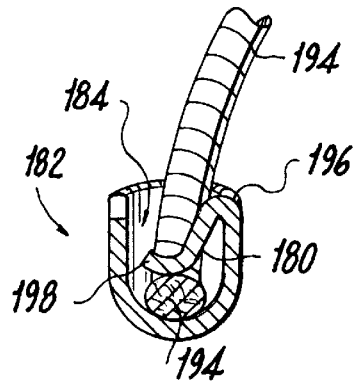
FIG. 29 is a cross-sectional view taken along line 29—29 of FIG. 28.

Referring now to FIGS. 28 and 29, in order to secure suture 194 within channel 184, suture 194 is placed within channel 184 and tab 180 is folded inwardly into channel 184. As tab 180 is folded inwardly, it forms a first bend 196 adjacent longitudinal side edge 172 and a second bend 198 which serves to secure suture 194 within channel 184.

It will be noted that the various apparatus engagement structure, described hereinabove, may be incorporated into channel-bodied surgical incision member 182 to facilitate handling by surgical suturing apparatus. In addition, it will be understood that the channel-bodied surgical incision member of FIGS. 27–30 alternatively could be made as a channel-bodied needle having a cutting edge at only one end thereof.

Figure 30:
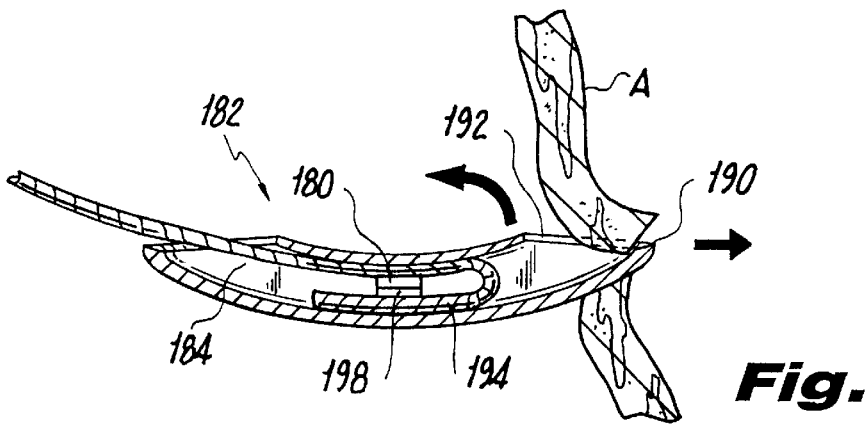
FIG. 30 is a side view, partly shown in section, illustrating the channel-bodied surgical incision member of FIG. 28 penetrating tissue.

As noted hereinabove, it is preferable to secure the length of suture material within the channel portion of a channel-bodied needle to facilitate passing the channel-bodied surgical needle or channel-bodied surgical incision member through tissue with minimal tissue damage. Thus, as shown in FIG. 30, as channel-bodied surgical incision member 182 is advanced into a tissue section, such as, for example, tissue section A, sharpened tip portion 190 penetrates tissue section A and cuts a flap of tissue therethrough. As channel-bodied surgical incision member 192 is further forced against tissue section A, suture 194 folds inwardly within channel 184 to facilitate passage through tissue section A. After surgical incision member 192 is pulled through tissue, the tissue flap closes against the suture to help seal the opening in the tissue surrounding the suture. As noted hereinabove, such cutting of an incision or flap of tissue may be preferable to creating a round or puncture wound within a tissue section with a needle of enlarged cross-section relative to the suture.

Figure 31:
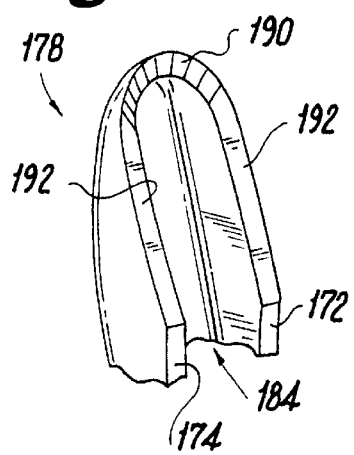
FIG. 31 is an enlarged perspective view of the tissue penetrating end of the channel-bodied surgical incision member of FIG. 28.
Figure 32:
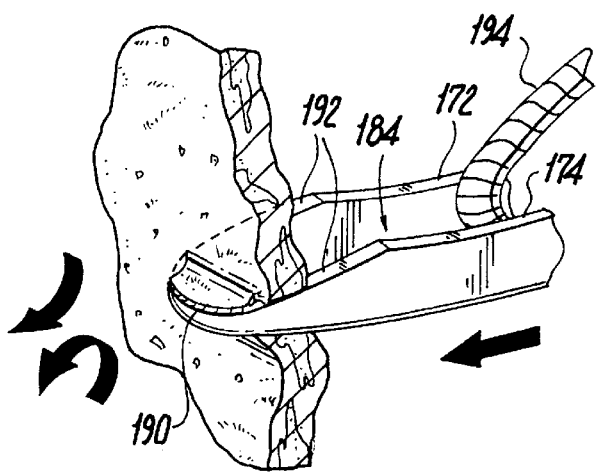
FIG. 32 is a perspective view, partly shown in section, illustrating the cutting tip of the channel-bodied surgical incision member penetrating tissue.

Referring for the moment to FIGS. 31 and 32, in any of the embodiments disclosed herein it may be preferable to have only a portion of transverse end edge 178 sharpened for cutting tissue. For example, it may be desirable to have only tip portion 190 sufficiently sharpened to cut tissue while tapered portions 192 spread or wedge open the incision made by sharpened tissue portion 190 to allow channel-bodied surgical incision member 182 to pass through a narrow flap of tissue.

Figure 33:
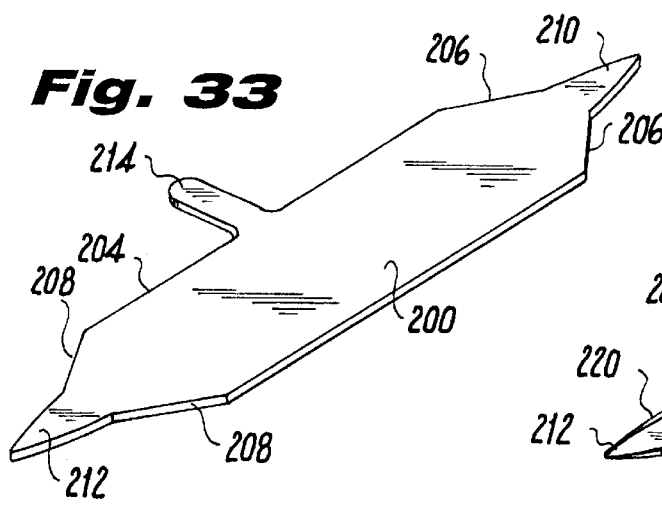
FIG. 33 is a perspective view of an alternate channel-bodied surgical needle blank incorporating alternate tissue penetrating structure.

Referring now to FIG. 33, there is shown a further alternate needle blank suitable for forming into channel-bodied surgical needles or channel-bodied surgical incision members. Alternate needle blank 200 generally includes first and second longitudinal side edges, 202 and 204, respectively, and tapered portions 206 and 208 at opposite ends of needle blank 200. Needle blank 200 is configured to provide unique tissue penetrating and cutting structure to facilitate the passage of a channel-bodied surgical needle or surgical incision member through tissue with minimal trauma. Thus, cutting end blanks 210 and 212 are formed projecting from tapered portions 206 and 208, respectively. Cutting end blanks 210 and 212 are provided to be ground or otherwise sharpened to formed penetrating tip portions on a channel-bodied surgical incision member or surgical needle. Tapered portions 206, 208 preferably also include cutting edges, but it is contemplated that cutting edges may not required on tapered portions 206, 208. It also is contemplated that a plurality of cutting end blanks may be provided. Additionally, needle blank 200 further includes suture attachment structure in the form of a tab 214 which functions substantially similar to tab 180 described hereinabove. Further, a channel-bodied surgical incision member formed from needle blank 200 may include various apparatus engagement structure as described hereinabove.

Figure 34:
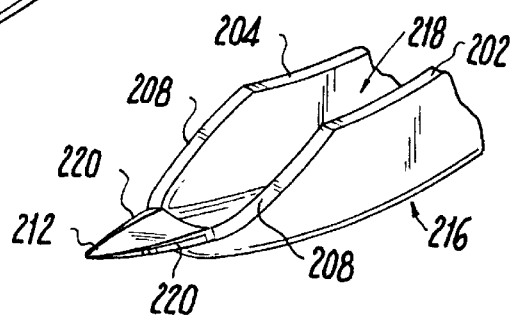
FIG. 34 is a perspective view of an end portion of a channel-bodied surgical incision member formed from the needle blank of FIG. 33 and incorporating the alternate tissue penetrating structure.

Referring now to FIG. 34, once needle blank 200 has been formed into a channel-bodied surgical incision member or surgical needle, such as, for example, channel-bodied surgical incision member 216, having a channel 218 formed therein, the cutting ends, such as, for example, cutting end 212 may be ground or otherwise sharpened to form sharp cutting edges 220. When needle blank 200 is formed into a channel-bodied surgical incision member or surgical needle, tapered edges 208 preferably remain unsharpened to avoid unnecessary cutting of tissue.

Figure 35:
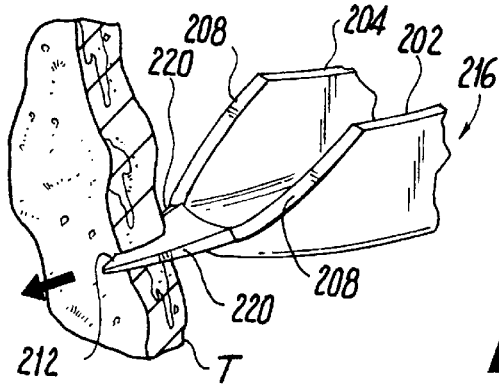
FIG. 35 is a perspective view of the penetrating tip portion of the channel-bodied surgical incision member of FIG. 34 initially penetrating tissue.
Figure 36:
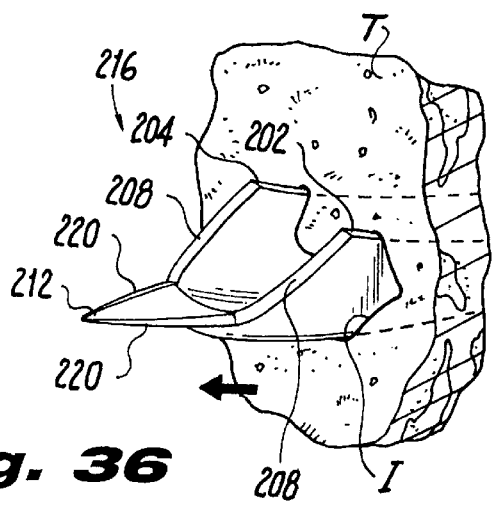
FIG. 36 is a perspective view similar to FIG. 35 and illustrating penetration of the channel-bodied surgical incision member through tissue.

As noted hereinabove, cutting ends 212 are provided to facilitate and enhance the cutting ability of end portions of a channel-bodied surgical incision member or surgical needle. Referring now to FIGS. 35 and 36, as cutting end 212 of channel-bodied surgical incision member 216 is forced into a tissue section T, cutting edges 220 cut tissue section T to form a narrow slit or incision therethrough. Thus, as shown in FIG. 36, when channel-bodied surgical incision member 216 is forced into tissue section T, tapered edges 208 wedge open the slit or incision I to provide a relatively narrow passageway for channel-bodied surgical incision member 216 to pass through the tissue section. Preferably, and as noted hereinabove, suture 194 will have been secured within channel-bodied surgical incision member 216 by means of tab 214. As channel-bodied surgical incision member 216 is moved through tissue section T, suture material 194 lies within channel 218 to minimize trauma to tissue section T surrounding incision I.

One advantage of the channel-bodied structure over a round-bodied structure includes lower drag as the channel-bodied needle passes through a tissue section. Also, as noted above the suture lays inside the needle for a smaller size entry hole and reduced tissue damage. This is especially appreciated during vascular tissue suturing. The entry point is a cut flap not a round hole.

It will be understood that various modifications may be made to the embodiments disclosed herein. For example, as noted, various other cross-sectional shapes may be imparted to the body portion of the channel-bodied structure as well as alternate straight or arcuate profiles. It is also contemplated the side walls may not be parallel, but may be inclined toward one another. Further, locations for the various apparatus engagement and suture attachment structure may be provided, for example, in the tissue penetrating end portions, etc. Additionally, it is contemplated to interchange the various apparatus engagement structures with the various cross-sections and methods of suture attachment. Other methods of securing a length of suture material within or to a channel-bodied needle is contemplated such as, for example, by welding, crimping, gluing or otherwise. Therefore, the above description should not be construed as limiting, but merely as exemplifications of preferred embodiments. Those skilled in the art will envision other modifications within the scope and spirit of the claims appended hereto.

What is claimed is:

1. A surgical needle comprising:
   a) a body portion having a substantially channel-shaped cross-section and defining a air of generally parallel sides, the channel-shaped cross-section extending along the entire length of the body portion; and
   b) a first tissue penetrating tip portion formed at one end of the body portion.

2. The surgical needle according to claim 1, wherein the penetrating tip portion has a substantially channel-shaped cross-section.

3. The surgical needle according to claim 1, wherein the penetrating tip portion has a leading edge and is beveled from a leading edge portion to the body portion to form a cutting edge thereon.

4. The surgical needle according to claim 1, further comprising a second tissue penetrating tip portion formed at an end of the body portion opposite the first tissue penetrating tip portion.

5. The surgical needle according to claim 1, further comprising apparatus engagement structure formed in the body portion.

6. The surgical needle according to claim 5, wherein the apparatus engagement structure is formed adjacent at least one end of the body portion.

7. The surgical needle according to claim 5, wherein the apparatus engagement structure includes an area of the body portion defining a hole therethrough.

8. The surgical needle according to claim 5, wherein the apparatus engagement structure includes an inwardly directed bulge formed in the body portion.

9. The surgical needle according to claim 5, wherein the apparatus engagement structure includes at least one recessed cross-sectional area portion formed in an outer surface of the body portion.

10. The surgical needle according to claim 1, further comprising suture attachment structure formed in the body portion and engagable with a length of suture material.

11. The surgical needle according to claim 10, wherein the suture attachment structure is formed intermediate ends of the body portion.

12. The apparatus according to claim 10, wherein the suture securement structure includes at least one reduced cross-sectional area portion formed in the body portion.

13. The apparatus according to claim 12, wherein the reduced area portion includes at least one inwardly directed bulge formed in a side of the body portion.

14. The apparatus according to claim 10, wherein the securement structure includes an inwardly direct flap formed from a side of the body portion.

15. The surgical needle according to claim 1, wherein the penetrating tip portion comprises tapered edges extending from the body of the needle and at least one pointed cutting end extending from the tapered edges and having at least one cutting surface thereon.

16. A method of suturing a tissue section comprising the steps of:
   a) providing a surgical needle having a substantially channel-shaped body portion extending throughout the entire length of the surgical needle and defining a pair of generally parallel side walls, and a length of suture material attached to the body portion;
   b) piercing a first tissue section with the surgical needle to cut a channel-shaped tissue flap; and
   c) drawing the surgical needle and a portion of the length of suture material through the channel-shaped flap of tissue.

17. The method according to claim 16, further comprising the steps of:
   a) piercing a second tissue section with the surgical needle to cut a second channel shaped flap in the tissue; and
   b) drawing the surgical needle and a portion of the length of suture material through the second channel shaped flap of tissue to thereby suture the tissue section and the second tissue section together.

18. The method according to claim 17 wherein the step of piercing a second tissue section comprises piercing a second tissue section with the opposite end of the needle used to pierce the first tissue section.

19. The method according to claim 16, wherein the tissue section to be pierced is a vascular tissue section.

20. A method of suturing a tissue section comprising the steps of:
   a) providing a surgical needle having a substantially channel-shaped body portion having generally parallel side walls and a length of suture material attached thereto;
   b) piercing a first tissue section with the surgical needle to cut a flat incision in tissue; and
   c) drawing the surgical needle and a portion of the length of suture material through the flat incision in tissue.

21. A surgical needle comprising:
   a) a body portion having a substantially channel-shaped cross-section extending the entire length thereof;
   b) apparatus engagement structure formed in the body portion, the apparatus engagement structure defining at least one opening formed through the body portion and transverse to a longitudinal axis thereof; and
   c) at least one cutting edge formed at a location adjacent to the body portion wherein the apparatus engagement structure includes at least one notch formed in a side wall of the body portion.

* * * * *